(12) United States Patent
Datta et al.

(10) Patent No.: US 11,285,295 B2
(45) Date of Patent: Mar. 29, 2022

(54) CONTROL HANDLE WITH DEVICE ADVANCING MECHANISM

(71) Applicant: BIOSENSE WEBSTER, INC., Irvine, CA (US)

(72) Inventors: Keshava Datta, Chino Hills, CA (US); Jeffrey William Schultz, Chino, CA (US)

(73) Assignee: BIOSENSE WEBSTER, INC., Irvine, CA (US)

( * ) Notice: Subject to any disclaimer, the term of this patent is extended or adjusted under 35 U.S.C. 154(b) by 323 days.

(21) Appl. No.: 16/363,954

(22) Filed: Mar. 25, 2019

(65) Prior Publication Data
US 2019/0217061 A1    Jul. 18, 2019

Related U.S. Application Data

(63) Continuation of application No. 15/408,361, filed on Jan. 17, 2017, now Pat. No. 10,238,838, which is a
(Continued)

(51) Int. Cl.
*A61M 25/01* (2006.01)
*A61B 17/34* (2006.01)
(Continued)

(52) U.S. Cl.
CPC ..... *A61M 25/0136* (2013.01); *A61B 17/3403* (2013.01); *A61M 25/0082* (2013.01);
(Continued)

(58) Field of Classification Search
CPC .......... A61M 25/0136; A61M 25/0082; A61M 25/0084; A61M 25/01; A61M 25/0147; A61M 25/09041; A61B 17/3403
See application file for complete search history.

(56) References Cited

U.S. PATENT DOCUMENTS

| 3,503,385 A | 3/1970 | Stevens |
| 4,391,199 A | 7/1983 | Morin |

(Continued)

FOREIGN PATENT DOCUMENTS

| EP | 1323448 A | 7/2003 |
| JP | 2002516729 | 6/2002 |

(Continued)

OTHER PUBLICATIONS

European Search Report for corresponding EP Application No. 08253145, dated Dec. 17, 2008, 3 pages.
(Continued)

*Primary Examiner* — Theodore J Stigell
(74) *Attorney, Agent, or Firm* — Lewis Roca Rothgerber Christie LLP

(57) ABSTRACT

A catheter having an internal advancing mechanism that can advance stiffening wires or other devices, has a catheter with a catheter body, a tip section distal the catheter body, a device extending through at least the catheter body, and a control handle proximal the catheter body, where the control handle has an advancing mechanism with a threaded member, an adjustment member, and a guided member to which the device is connected, and the advancing mechanism is configured to advance and retract the device along the catheter body as controlled by a user. Each of the threaded member and the adjustment member has a generally cylindrical configuration. The threaded member has an outer surface configured with a helical guide channel. The adjustment member is configured to guide the guided member to move within the helical guide channel to advance and retract the device. The adjustment member can be rotatable over the threaded member by the user to control advancement and retraction of the device. The device may be a stiffener wire,
(Continued)

a needle or any other device suitable for advancement and retraction in a catheter.

20 Claims, 10 Drawing Sheets

Related U.S. Application Data continuation of application No. 14/981,393, filed on Dec. 28, 2015, now Pat. No. 9,545,500, which is a continuation of application No. 14/060,517, filed on Oct. 22, 2013, now Pat. No. 9,220,531, which is a continuation of application No. 13/085,351, filed on Apr. 12, 2011, now Pat. No. 8,562,568, which is a continuation of application No. 11/863,149, filed on Sep. 27, 2007, now Pat. No. 7,935,082.

(51) Int. Cl.
*A61M 25/09* (2006.01)
*A61M 25/00* (2006.01)

(52) U.S. Cl.
CPC ........ *A61M 25/0084* (2013.01); *A61M 25/01* (2013.01); *A61M 25/0147* (2013.01); *A61M 25/09041* (2013.01)

(56) References Cited

U.S. PATENT DOCUMENTS

| | | | |
|---|---|---|---|
| 5,114,414 A | 5/1992 | Buchbinder | |
| 5,185,004 A | 2/1993 | Lashinski | |
| 5,275,151 A | 1/1994 | Shockey et al. | |
| 5,306,272 A * | 4/1994 | Cohen | A61B 90/11 403/370 |
| 5,327,906 A | 7/1994 | Fideler | |
| 5,336,222 A | 8/1994 | Durgin, Jr. et al. | |
| 6,027,462 A | 2/2000 | Greene et al. | |
| 6,059,739 A | 5/2000 | Baumann | |
| 6,165,164 A | 12/2000 | Hill et al. | |
| 6,179,809 B1 * | 1/2001 | Khairkhahan | A61M 25/0084 604/528 |
| 6,530,913 B1 | 3/2003 | Giba et al. | |
| 6,540,725 B1 | 4/2003 | Ponzi | |
| 6,607,511 B2 | 8/2003 | Halseth | |
| 7,399,294 B2 | 7/2008 | Mickley | |
| 7,416,547 B2 | 8/2008 | Hill et al. | |
| 2002/0120250 A1 * | 8/2002 | Altman | A61M 25/0084 604/508 |
| 2002/0183720 A1 | 12/2002 | Hill et al. | |
| 2003/0032927 A1 | 2/2003 | Halseth et al. | |
| 2003/0187396 A1 | 10/2003 | Ponzi | |
| 2003/0195467 A1 * | 10/2003 | Mickley | A61M 25/0084 604/117 |
| 2003/0195470 A1 | 10/2003 | Ponzi | |
| 2004/0010231 A1 | 1/2004 | Leonhardt et al. | |
| 2004/0158229 A1 | 8/2004 | Quinn | |
| 2006/0142694 A1 * | 6/2006 | Bednarek | A61M 25/0136 604/95.04 |
| 2006/0161199 A1 | 7/2006 | Peterson | |
| 2006/0200079 A1 | 9/2006 | Magnusson | |
| 2007/0118201 A1 | 5/2007 | Pappas et al. | |
| 2007/0156224 A1 | 7/2007 | Cioanta et al. | |

FOREIGN PATENT DOCUMENTS

| | | |
|---|---|---|
| JP | 2004505688 | 2/2004 |
| JP | 2005526526 | 9/2005 |
| WO | WO9962585 A1 | 12/1999 |

OTHER PUBLICATIONS

JP Office action dated Nov. 13, 2012 for JP Application No. 2008-249752, 4 pages.

* cited by examiner

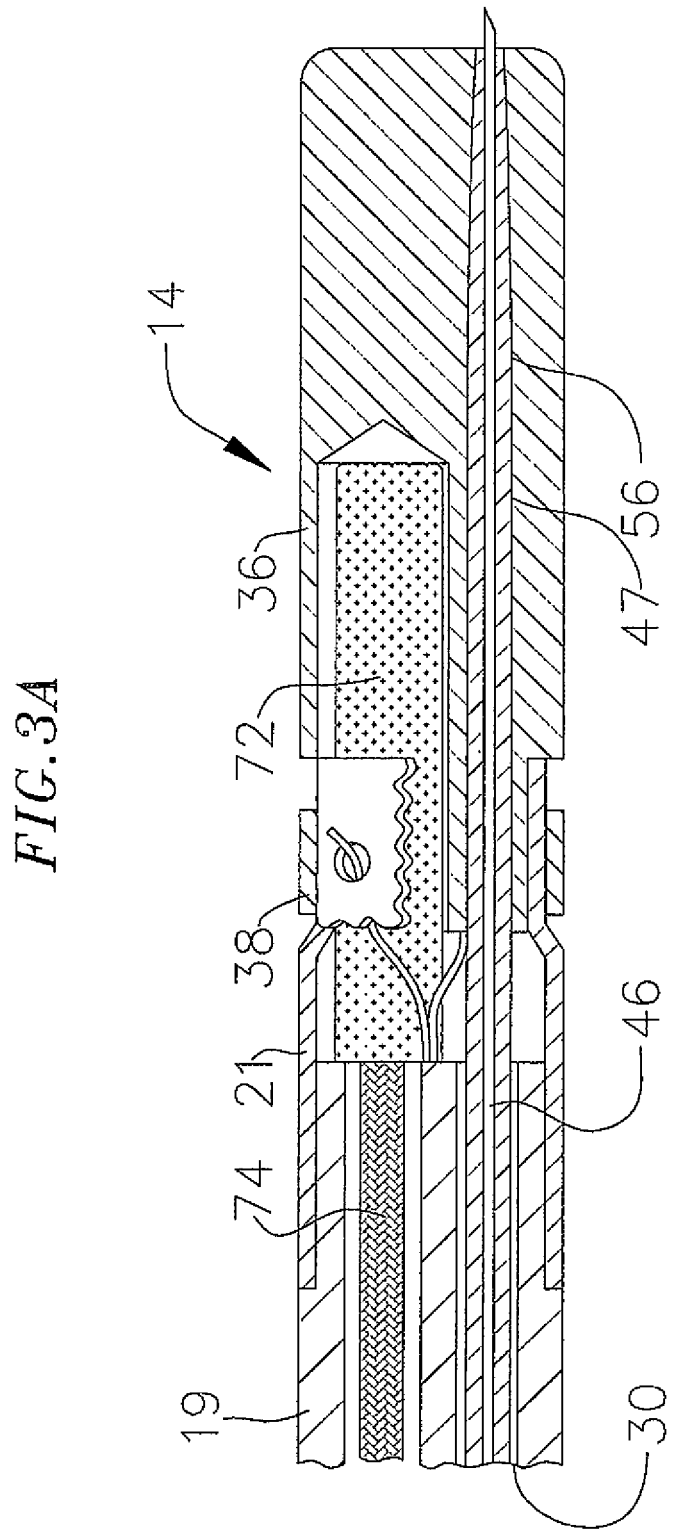

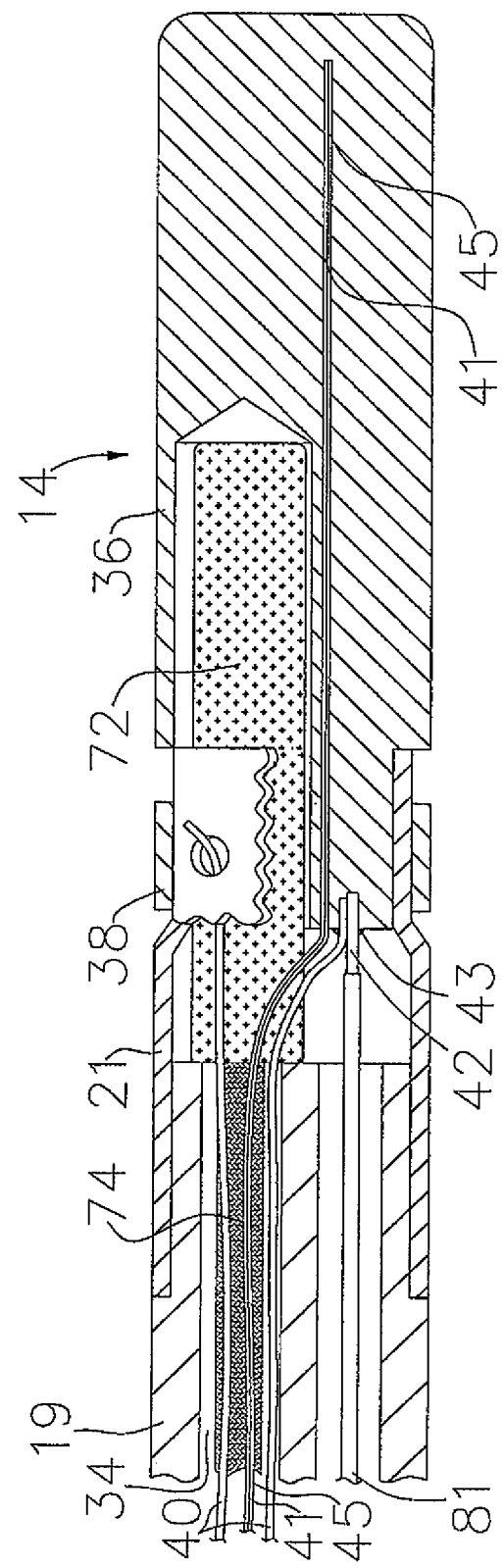

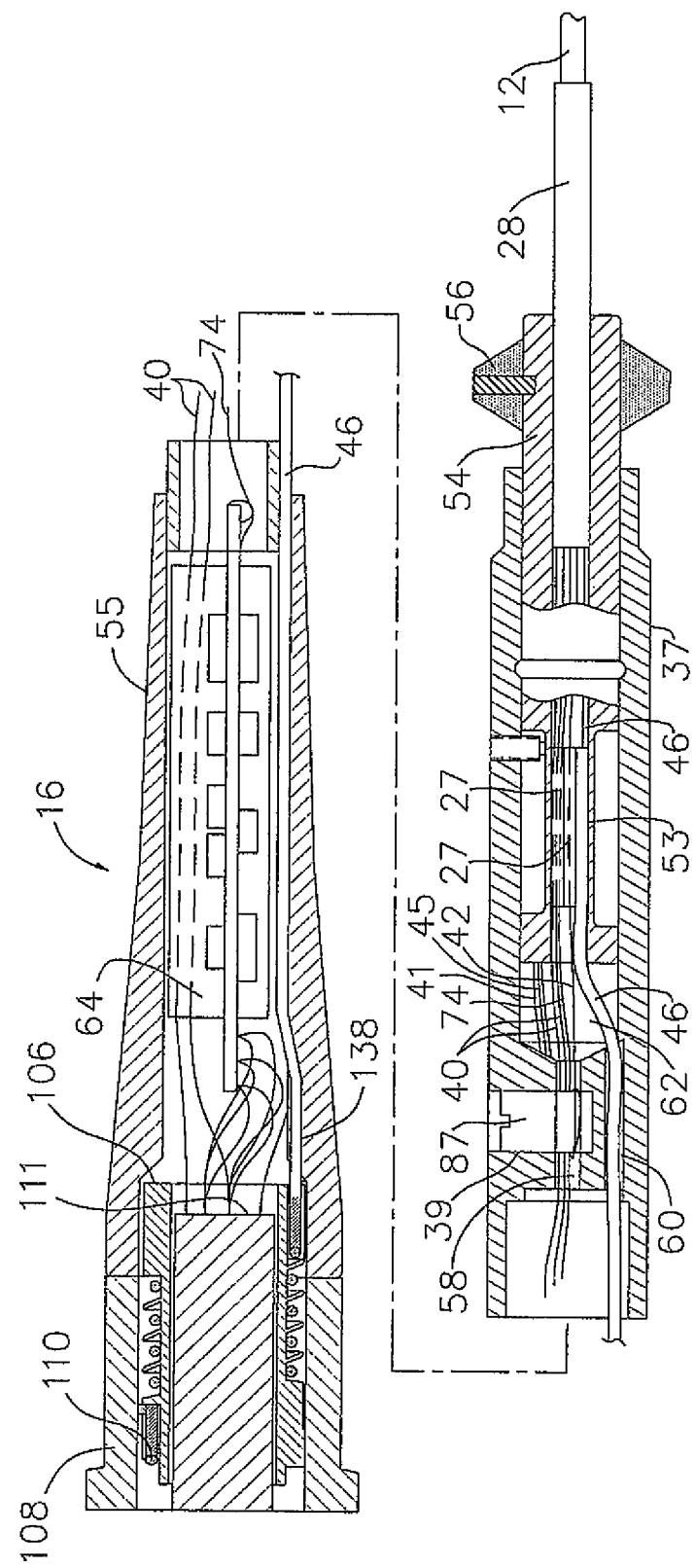

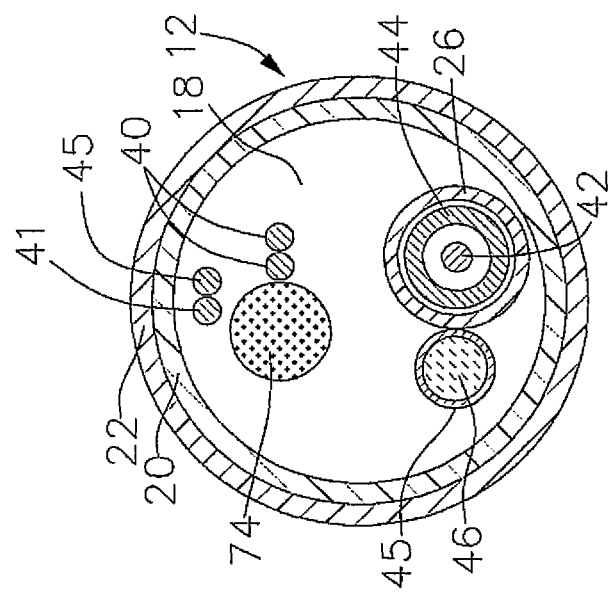
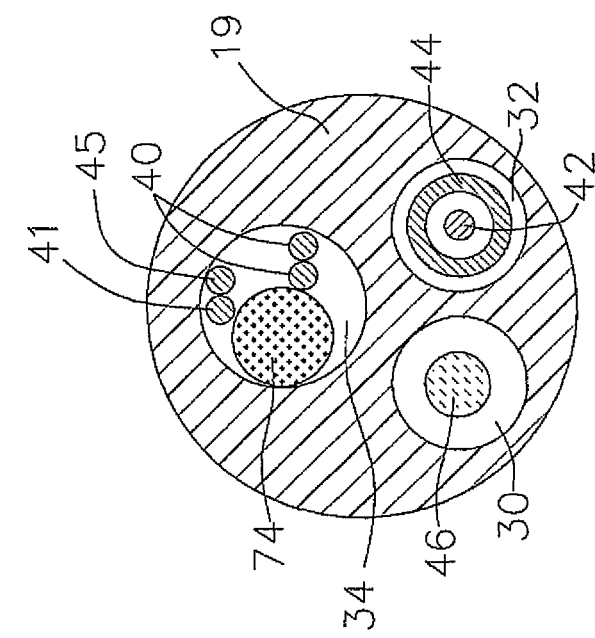

CONTROL HANDLE WITH DEVICE ADVANCING MECHANISM

CROSS REFERENCE TO RELATED APPLICATION(S)

This application is a continuation of and claims priority to and the benefit of U.S. patent application Ser. No. 15/408,361 filed Jan. 17, 2017, issued as U.S. Pat. No. 10,238,838, which is a continuation of and claims priority to and the benefit of U.S. patent application Ser. No. 14/981,393 filed Dec. 28, 2015, issued as U.S. Pat. No. 9,545,500, which is a continuation of and claims priority to and the benefit of U.S. patent application Ser. No. 14/060,517 filed Oct. 22, 2013, issued as U.S. Pat. No. 9,220,531, which is a continuation of and claims priority to and the benefit of U.S. patent application Ser. No. 13/085,351 filed Apr. 12, 2011, now U.S. Pat. No. 8,562,568, which is a continuation of and claims priority to and the benefit of U.S. patent application Ser. No. 11/863,149 filed Sep. 27, 2007, now U.S. Pat. No. 7,935,082, the entire contents of all of which are incorporated herein by reference.

FIELD OF INVENTION

The present invention relates to catheters, in particular, Electro-Physiology (EP) catheters with a control handle and a lumened catheter body.

BACKGROUND OF INVENTION

Catheter shafts are generally made of flexible, bio-compatible material, such as plastic, including polyethylene, polyester or polyamide. However, advancement into and through a patient's body and manipulation of a catheter can be difficult if the catheter shaft lacks a certain amount of stiffness. Moreover, it can be particularly challenging to provide suitable flexibility, particularly near the shaft tip, while maintaining adequate overall shaft stiffness. While there are devices available to provide or add stiffness to catheters, including stiffener wires, they are typically separate and not integrated in the catheter such that separate handling and manipulation are required. Indeed, there are few, if any, known mechanism internal to the catheter that can advance stiffening wires or other devices into, or through, EP catheters. It is therefore desirable to provide a catheter having an internal advancing mechanism that can advance stiffening wires or other devices into or through the catheter shaft.

SUMMARY OF THE INVENTION

The present invention may be directed to a wide variety of Electro-Physiology (EP) catheters (floppy shaft and/or multi-profile) that have applications for the advancement of a stiffening wire, needle or any other device. In one embodiment, there is provided a catheter with a catheter body, a tip section and a device extending through at least the catheter body, where a control handle has an advancing mechanism with a threaded member, an adjustment member, and a guided member therebetween to which the device is connected, to advance and retract the device along the catheter body as controlled by a user.

It is further provided that each of the threaded member and the adjustment member, both of which are generally cylindrical, are coupled to each other with the guided member between an inner surface of the adjustment member and an outer surface of the threaded member, with the guided member riding in a helical guide channel formed in the outer surface of the threaded member. The adjustment member is rotatable over the threaded member by the user to move the guided member in the channel thereby controlling the advancement and retraction of the device attached to the guided member. Rotation in one direction advances the device along the catheter body and rotation in the opposition direction retracts the device. The device may be a stiffener wire, a needle or any other device suitable for advancement and retraction in a catheter.

In a more detailed embodiment, there is provided a catheter having a catheter body, a tip section, a control handle comprising a threaded member, an adjustment member mounted on the threaded member and a guided member situated therebetween, and a device connected to the guided member and extending distally therefrom through the control handle, the catheter body and the tip section. The adjustment member is configured for rotation relative to the threaded member by a user to advance and retract the device. The device is wound about the threaded member and adapted to unwind and rewind as guided by the guided member in response to rotation of the adjustment member relative to the threaded member by a user.

BRIEF DESCRIPTION OF THE DRAWINGS

These and other features and advantages of the present invention will be better understood by reference to the following detailed description when considered in conjunction with the accompanying drawings wherein:

FIG. 3A is a side cross-sectional view of an embodiment of the tip section, including the tip section, taken along a first diameter.

FIG. 3B is a side cross-sectional view of an embodiment of the tip section, taken along a second diameter generally perpendicular to the first diameter.

FIG. 4 is a side cross-sectional view of an embodiment of a catheter handle.

FIG. 5 is a longitudinal cross-sectional view of the catheter body of FIG. 2, taken generally along line 5-5.

FIG. 6 is a longitudinal cross-sectional view of the tip section of FIG. 2, taken generally along line 6-6.

DETAILED DESCRIPTION OF THE INVENTION

Figure 1:
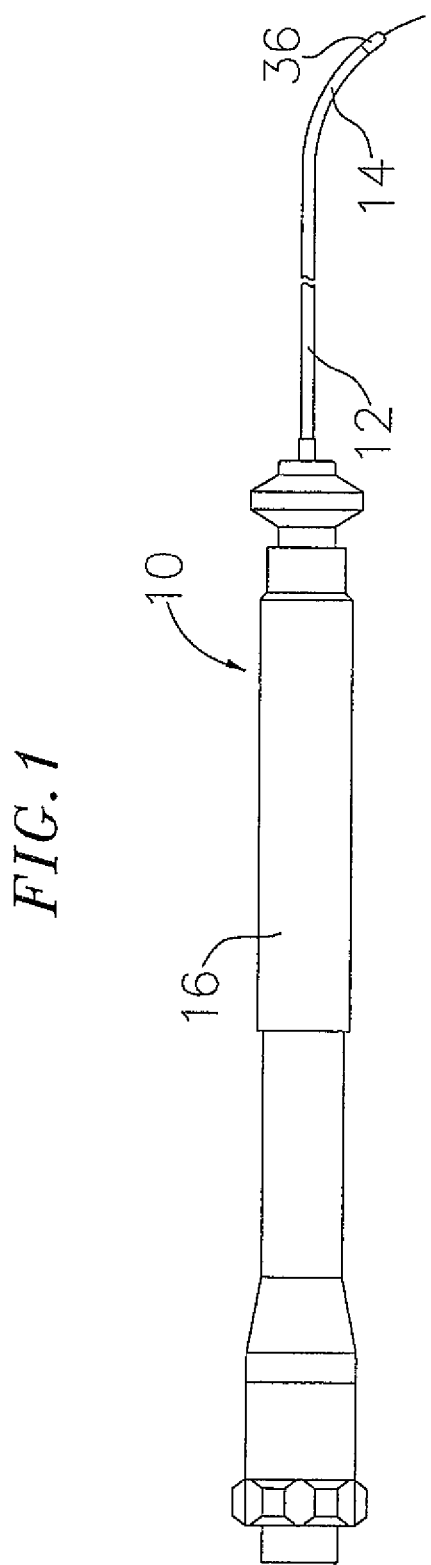
FIG. 1 is a side view of an embodiment of a catheter of the present invention.

With reference to FIG. 1, there is provided a catheter (for example, an Electro-Physiology (EP)) catheter 10 adapted to advance and retract a device 46 (for example, a wire, a needle, infusion tube or the like) in the catheter. The catheter comprises an elongated catheter body 12 having proximal and distal ends, a tip section 14 at the distal end of the catheter body 12, and a control handle 16 having a threaded advancing mechanism 17 controllable by a user to move the device distally and proximally in the catheter body.

Figure 2:
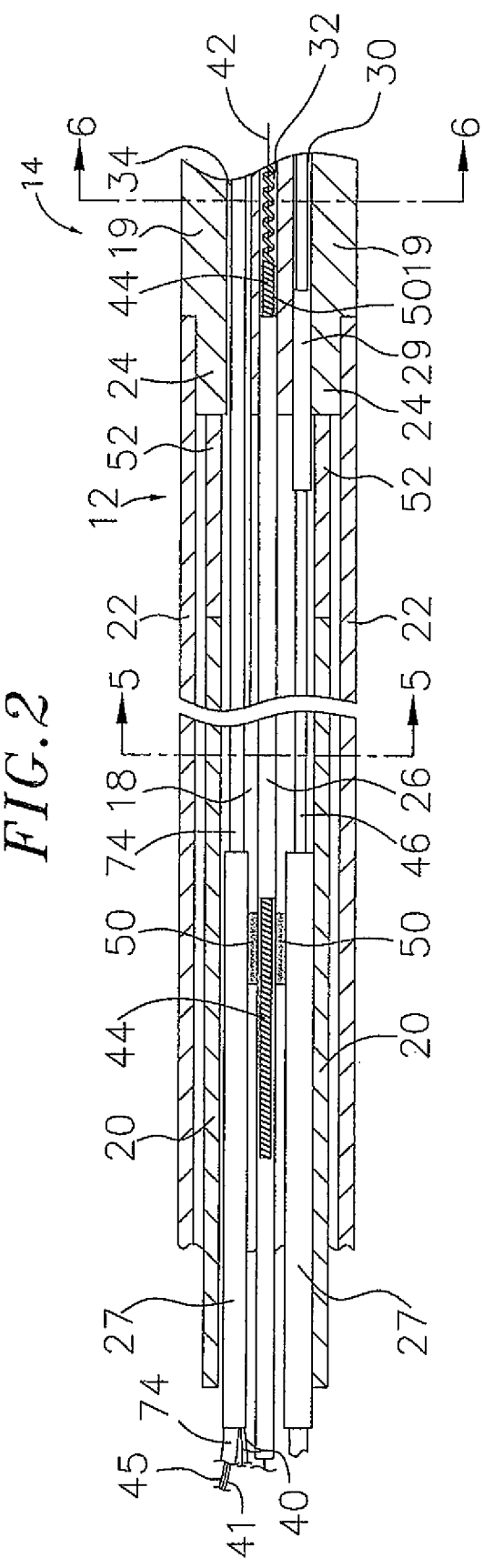
FIG. 2 is a side cross-sectional view of an embodiment of a catheter body, including the junction between the catheter body and a tip section.

With reference to FIGS. 2 and 5, the catheter body 12 comprises an elongated tubular construction having a single, central or axial lumen 18. The catheter body 12 is flexible, i.e., bendable, but substantially non-compressible along its length. The catheter body 12 can be of any suitable construction and made of any suitable material. One construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical. Likewise the thickness of the outer wall 22 is not critical. The inner surface of the outer wall 22 is lined with a stiffening tube 20, which can be made of any suitable material, for example, polyimide. The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used As shown in FIGS. 2 and 6, the tip section 14 comprises a short section of tubing 19 having three lumens. The tubing 19 is made of a suitable non-toxic material which can be more flexible than the catheter body 12. One material for the tubing 19 is braided polyurethane, i.e., polyurethane with an embedded mesh of braided stainless steel or the like. The outer diameter of the tip section 14, like that of the catheter body 12. The size of the lumens is not critical. In one embodiment, the first lumen 30 and second lumen 32 are generally about the same size, with the third lumen 34 having a slightly larger diameter.

One embodiment of means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by glue or the like. In the arrangement shown, a spacer 52 lies within the catheter body 12 between the distal end of the stiffening tube 20 and the proximal end of the tip section 14. The spacer 52 can be made of a material which is stiffer than the material of the tip section 14, e.g., polyurethane, but not as stiff as the material of the stiffening tube 20, e.g., polyimide. A spacer made of Teflon® may be used in one embodiment. The spacer 52 may have an outer and inner diameter about the same as the outer and inner diameters of the stiffening tube 20. The spacer 52 provides a transition in flexibility at the junction of the catheter body 12 and catheter tip 14, which allows the junction of the catheter body 12 and tip section 14 to bend smoothly without folding or kinking.

The spacer 52 is held in place by the stiffening tube 20. The stiffening tube 20, in turn, is held in place relative to the outer wall 22 by glue joints at the proximal end of the catheter body 12.

As shown in FIGS. 2 and 5, extending through the single lumen 18 of the catheter body 12 are lead wires 40, the device 46, a sensor cable 74, and a compression coil 44 through which a puller wire 42 extends. A single lumen 18 catheter body compared to a multi-lumen body can permit better tip control when rotating the catheter 10. The single lumen 18 permits the lead wires 40, the device 46, the sensor cable 74, and the puller wire 42 surrounded by the compression coil 44 to float freely within the catheter body. If such components were restricted within multiple lumens, they can tend to build up energy when the handle 16 is rotated, resulting in the catheter body 12 having a tendency to rotate back if, for example, the handle is released, or if bent around a curve, to flip over, either of which are often undesirable performance characteristics.

The puller wire 42 is anchored at its proximal end to the control handle 16 and anchored at its distal end to the tip section 14. The puller wire 42 is made of any suitable metal, such as stainless steel or Nitinol, and is coated with Teflon® or the like. The coating imparts lubricity to the puller wire 42.

The compression coil 44 extends from the proximal end of the catheter body 12 to the proximal end of the tip section 14. The compression coil 44 is made of any suitable metal, such as stainless steel. The compression coil 44 is tightly wound on itself to provide flexibility, i.e., bending, but to resist compression. The inner diameter of the compression coil 44 is slightly larger than the diameter of the puller wire 42. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and any of the lead wires 40, the device 46 or sensor cable 74. A non-conductive sheath 26 made of polyimide tubing can be provided.

The compression coil 44 is anchored at its proximal end to the proximal end of the stiffening tube 20 in the catheter body 12 by a glue joint and at its distal end to the tip section 14 at a location distal to the spacer 52 by glue joint 50. Both glue joints may comprise polyurethane glue or the like. The glue may be applied by means of a syringe or the like through a hole made between the outer surface of the catheter body 12 and the single lumen 18. Such a hole may be formed, for example, by a needle or the like that punctures the wall of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil 44.

As shown in FIGS. 2, and 6, the puller wire 42 extends into the second lumen 32 of the tip section 14. The puller wire 42 is anchored to a tip electrode 36 or to the side of the catheter tip section 14. Within the tip section 14, and distal to the glue joint 51, the turns of the compression coil are expanded longitudinally. Such expanded turns are both bendable and compressible. The puller wire 42 extends through the expanded turns then into a plastic, such as Teflon®, sheath 81 (FIG. 3B), which prevents the puller wire 42 from cutting into the wall of the tip section 14 when the tip section 14 is deflected.

Figure 9:
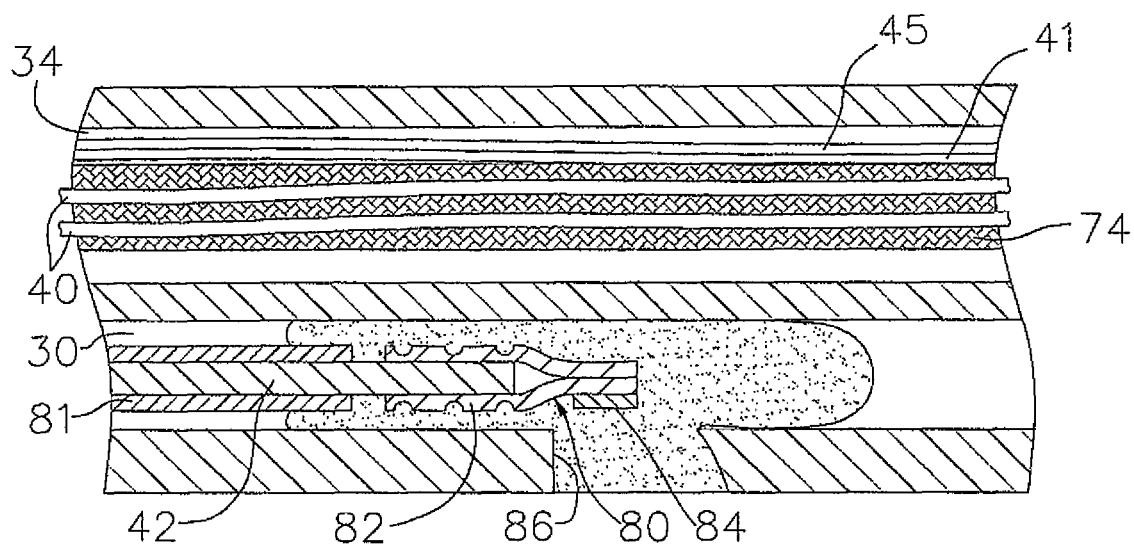
FIG. 9 is a cross-sectional view of a portion of the catheter tip section showing a means for anchoring the puller wire.
Figure 10:
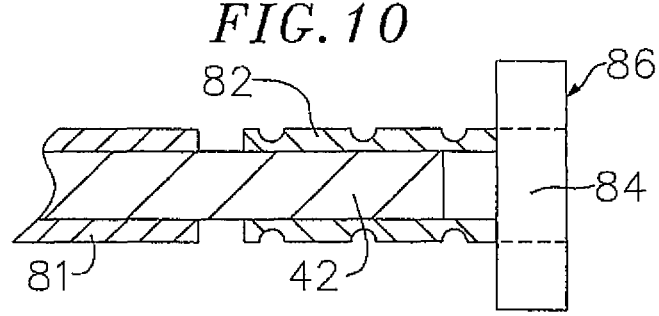
FIG. 10 is a top cross-sectional view of a preferred puller wire anchor.
Figure 11:
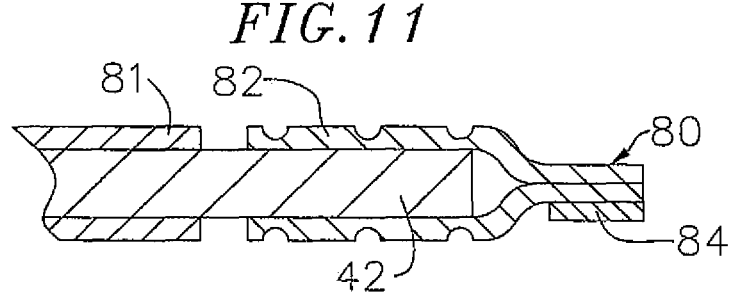
FIG. 11 is a side cross-sectional view of a preferred puller wire anchor.

As shown in FIG. 3B, the distal end of the puller wire 42 may be anchored to the tip electrode 36 by solder or the like, as shown in FIG. 2b or to the side wall of the tip section 14. If attached to the side wall, an embodiment comprising an anchor 80 fixedly attached to the distal end of the puller wire 42 is be used, as illustrated in FIGS. 9-11. In such an embodiment, the anchor is formed by a metal tube 82, e.g., a short segment of hypodermic stock, which is fixedly attached, e.g., by crimping, to the distal end of the puller wire 42. The tube 82 has a section which extends a short distance beyond the distal end of the puller wire 42. A cross-piece 84 made of a small section of stainless steel ribbon or the like is soldered or welded in a transverse arrangement to the distal end of the tube 82, which is flattened during the operation. This creates a T-bar anchor 80. A notch 86 is created in the side of the catheter tip section 14 resulting in an opening into the second lumen 32 carrying the puller wire 42. The anchor 80 lies within the notch 86. Because the length of the ribbon forming the cross-piece 84 is longer than the diameter of the opening into the second lumen 32, the anchor 80 cannot be pulled completely into the second lumen 32. The notch 86 is then sealed with polyurethane or the like to give a smooth outer surface.

With reference to FIGS. 3A and 3B, at the distal end of the tip section 14 is a tip electrode 36. In the illustrated embodiment, the tip electrode 36 has a diameter about the same as the outer diameter of the tubing 19. The tip electrode 36 is connected to the tubing 19 by means of a plastic housing 21, which can be made of polyetheretherketone (PEEK). The proximal end of the tip electrode 36 is notched circumferentially and fits inside the distal end of the plastic housing 21 and is bonded to the housing 21 by polyurethane glue or the like. The proximal end of the plastic housing 21 is bonded with polyurethane glue or the like to the distal end of the tubing 19 of the tip section 14.

Mounted on the distal end of the plastic housing 21 is a ring electrode 38. The ring electrode 38 is slid over the plastic housing 21 and fixed in place by glue or the like. If desired, additional ring electrodes may be used and can be positioned over the plastic housing 21 or over the flexible tubing 19 of the tip section 14.

The tip electrode 36 and ring electrode 38 are each connected to separate lead wires 40. The lead wires 40 extend through the third lumen 34 of tip section 14, the catheter body 12, and the control handle 16, and terminate at their proximal end in an input jack (not shown) that may be plugged into an appropriate monitor (not shown). If desired, the portion of the lead wires 40 extending through the catheter body 12, control handle 16 and proximal end of the tip section 14 may be enclosed or bundled within a protective tube or sheath.

The lead wires 40 are attached to the tip electrode 36 and ring electrode 38 by any conventional technique. Connection of lead wire 40 to the tip electrode 36 can be accomplished by weld 43, as shown in FIG. 3B. Connection of a lead wire 40 to a ring electrode 38 can be accomplished by first making a small hole through the plastic housing 21. Such a hole can be created, for example, by inserting a needle through the plastic housing 21 and heating the needle sufficiently to form a permanent hole. A lead wire 40 is then drawn through the hole by using a microhook or the like. The ends of the lead wire 40 are then stripped of any coating and soldered or welded to the underside of the ring electrode 38, which is then slid into position over the hole and fixed in place with polyurethane glue or the like.

In the illustrated embodiment, a temperature sensing means is provided for the tip electrode 36 and, if desired, the ring electrode 38. Any conventional temperature sensing means, e.g., a thermocouple or thermistor, may be used. With reference to FIG. 3B, one temperature sensing means for the tip electrode 36 comprises a thermocouple formed by an enameled wire pair. One wire of the wire pair is a copper wire 41, e.g., a number 40 copper wire which acts not only as part of the thermocouple, but as the electrode lead. The other wire of the wire pair is a construction wire 45, e.g., a number 40 construction wire, which gives support and strength to the wire pair. The wires 41 and 45 of the wire pair are electrically isolated from each other except at their distal ends where they contact and are welded or soldered to the tip electrode 36. Because it is desirable to monitor the temperature of the tip electrode 36 at a site adjacent the distal end of the optic fiber 46, the thermocouple with a blind hole in the tip electrode 36 is fixed to the tip electrode 36 at the distal end of the blind hole as shown. The wires 41 and 45 extend through the third lumen 34 of the tip section 14 and through the central lumen 18 of the catheter body 12 into the control handle 16.

In the illustrated embodiment, an electromagnetic sensor 72 is contained within the distal end of the tip section 14. The electromagnetic sensor 72 is connected by means of electromagnetic sensor cable 74, which extends through the third lumen 34 of the tip section 14 and through the catheter body 12 into the control handle 16. The electromagnetic sensor cable 74 comprises multiple wires encased within a plastic covered sheath. In the control handle 16, the wires of the sensor cable 74 are connected to a circuit board 64. The circuit board 64 amplifies the signal received from the electromagnetic sensor and transmits it to a computer in a form understandable by the computer. Also, because the catheter is designed for single use only, the circuit board contains an EPROM chip which shuts down the circuit board after the catheter has been used. This prevents the catheter, or at least the electromagnetic sensor, from being used twice. A suitable electromagnetic sensor is described, for example, in U.S. Pat. No. 4,391,199, which is incorporated herein by reference. An electromagnetic mapping sensor 72 is manufactured by Biosense Ltd. Israel and marketed under the trade designation NOGA.

The electrode lead wires 40, thermocouple wires 41 and 45, and electromagnetic sensor cable 74 and any other components or device, including the device 46, are allowed longitudinal movement within the catheter body 12. The wires 40, 41 and 45 and cable 74 are allowed such movement so that they do not break when the tip section 14 is deflected. The device 26 is allowed such movement so that it can be advanced and retracted in accordance with a feature of the present invention. To provide for such lengthwise movement, there are tunnels provided through the glue joint 50 in the catheter body 12 (FIG. 2), which fixes the proximal end of the compression coil 44 inside the catheter body 12. The tunnels are formed by transfer tubes 27, made of short segments of polyimide tubing in one embodiment. In the embodiment shown in FIG. 2, there is one transfer tube 27 for the wires 40, 41 and 45 and the electromagnetic sensor cable 74 and a second transfer tube 27 for the device 46. It is understood that the number of transfer tubes may vary as desired.

Longitudinal movement of the puller wire 42 relative to the catheter body 12, which results in deflection of the tip section 12, is accomplished by suitable manipulation of the control handle 16. As shown in FIG. 4, the distal end of the control handle 16 comprises a piston 54 with a thumb control 56 for manipulating the puller wire 42. The proximal end of the catheter body 12 is connected to the piston 54 by means of a shrink sleeve 28.

The puller wire 42, lead wires 40, thermocouple wires 41 and 45, device 46 and electromagnetic sensor cable 74 extend through the piston 54. The piston 54 lies within a barrel 57 of the control handle. The barrel 57 is generally solid having a piston chamber for receiving the piston 54. Extending proximally from the piston chamber are two longitudinal tunnels 58 and 60 and a transverse hole 59 for receiving the anchor pin 87. The first longitudinal tunnel 58 is in communication with the transverse hole 59. The lead wires 40, thermocouple wires 41 and 45, and sensor cable 74 extend through the first tunnel 58. The puller wire 42 also extends through the first tunnel 58 and is anchored to the anchor pin 87 in the transverse hole 59. The device 46 extends through the second tunnel 60. Between the distal end of the tunnels 58 and 60 and the proximal end of the piston 54, chamber 62 provides additional space to avoid undesirable bending of the components extending therethrough. The electromagnetic sensor cable 74 connects to the circuit board 64 in the control handle 16. Wires 90 connect the circuit board 64 to a computer and imaging monitor (not shown).

The device 46, for example, a stiffener wire, a needle, or the like, extends through the control handle 16 and catheter body 12 and into the first lumen 30 of the tip section 14. In accordance with a feature of the present invention, the device 46 can be moved distally and proximally within catheter body by manipulation of the control handle 16, as discussed further below. Where the device is a stiffener wire or the like, the stiffener wire can be controlled to slide distally and proximally within the catheter body and/or tip section. Where the device 46 is a needle or the like, its distal end can be advanced beyond the distal end of the tip section to reach and contact tissue separately from the tip section, and then retracted back into tip section. As understood by one of ordinary skill in the art, the device 46 is not limited to stiffener wires and needles, but includes any structure that may be advanced within a catheter.

Figure 7:
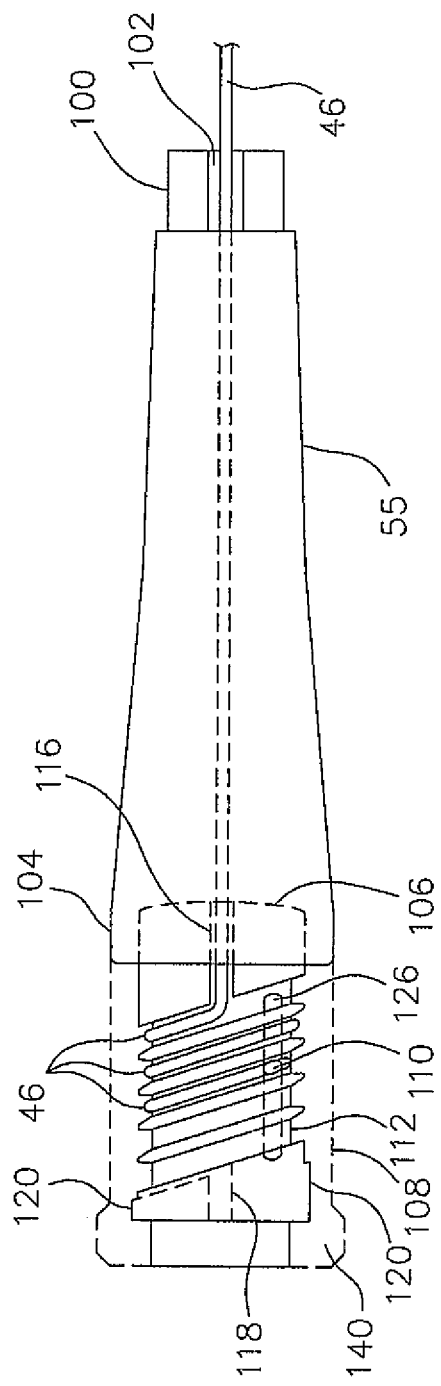
FIG. 7 is a top view of the catheter handle.
Figure 8:
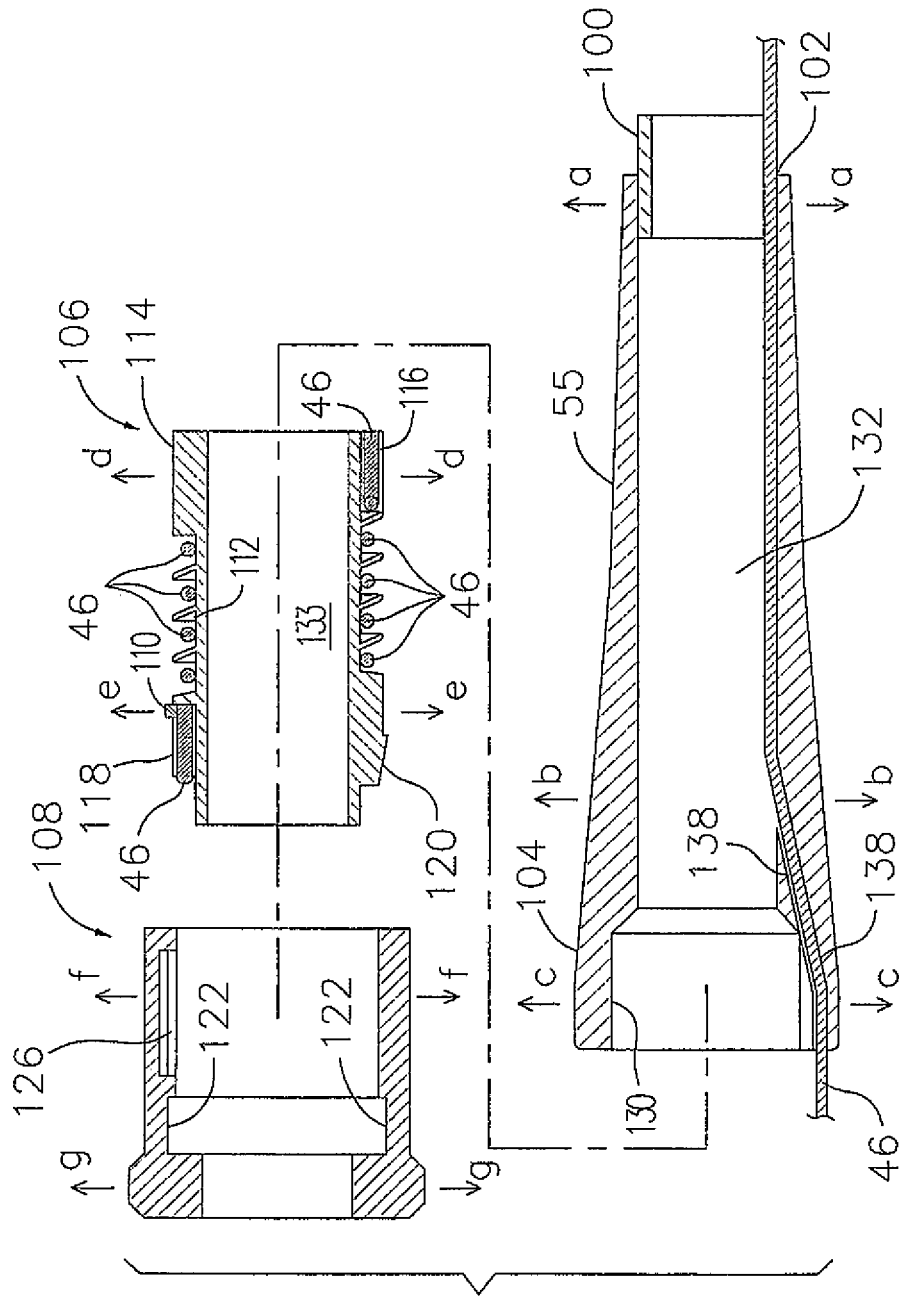
FIG. 8 is a side cross-sectional view of an advancing mechanism and a barrel of the control handle.
Figure 8A:
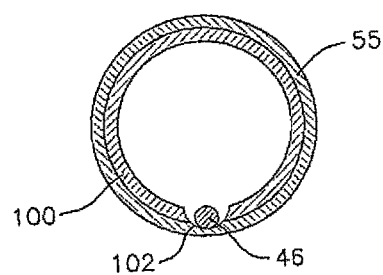
FIG. 8A is a longitudinal cross-sectional view of the barrel of FIG. 8, taken along line a-a.
Figure 8B:
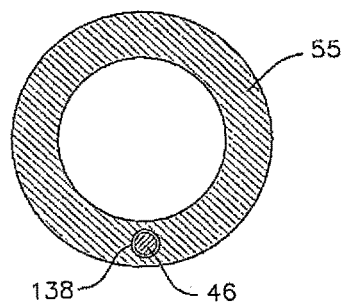
FIG. 8B is a longitudinal cross-sectional view of the barrel of FIG. 8, taken along line b-b.
Figure 8C:
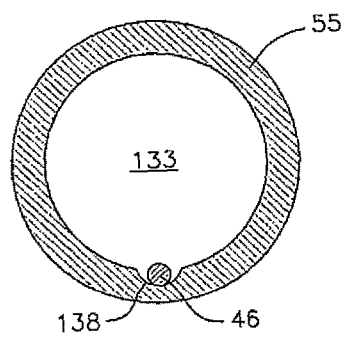
FIG. 8C is a longitudinal cross-sectional view of the barrel of FIG. 8, taken along line c-c.

In the illustrated embodiment of FIGS. 4, 7 and 8, the control handle 16 has a second barrel 55 proximal the barrel 57 for an extended control handle configuration. The device 46 extends proximally into the control handle through the piston 54 in the distal barrel 57, and through a distal end 100 of the proximal barrel 55 which has an opening or notch 102 in its general circular cross section (FIG. 5a) to accommodate the device 46. In the illustrated embodiment, the advancing mechanism 17, as means for allowing the advance and retraction of the device 46 in accordance with a feature of the present invention, is mounted on a proximal end 104 of the proximal barrel 55.

Figure 8D:
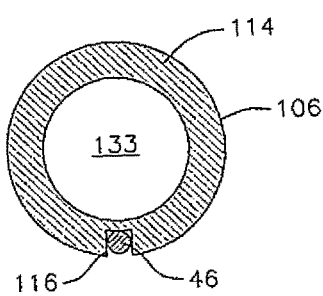
FIG. 8D is a longitudinal cross-sectional view of a threaded member of FIG. 8, taken along line d-d.
Figure 8E:
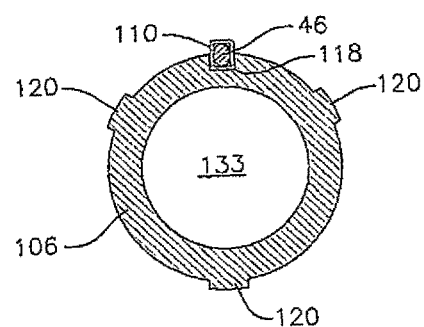
FIG. 8E is a longitudinal cross-sectional view of the threaded member of FIG. 8, taken along line e-e.
Figure 8F:
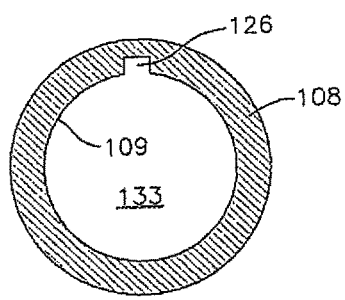
FIG. 8F is a longitudinal cross-sectional view of an adjustment member of FIG. 8, taken along line f-f.
Figure 8G:
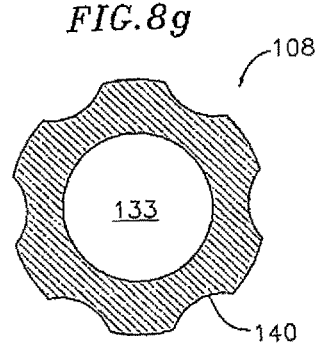
FIG. 8G is a longitudinal cross-section view of the adjustment member of FIG. 8, taken along line g-g.

In the illustrated embodiment, the device advancing mechanism 17 includes a generally cylindrical threaded guide member 106, a generally cylindrical adjustment member 108 mounted thereon, and a guided member 110 (e.g., a slug or pin) situated between an outer surface 114 of the member 106 and an inner surface 109 of the member 108. The guided member slides in a helical guide channel 112, with a generally straight distal portion 116 and a generally straight proximal portion 118, all formed on the outer surface 114 of the guide member 106. In the illustrated embodiment, the helical guide channel 112 winds about the guide member 106 for approx. 4-½ turns, such that the distal channel portions 116 and 118 are generally diametrical of each other (see FIGS. 8d and 8e).

The generally cylindrical adjustment member 108 is sized such that its interior is in close conformity with the member 106 to receive the latter in an overlapping, generally co-axial configuration. In that regard, the guide member 106 has protrusions 120 that lock with a recessed ring 122 formed in the inner surface 109 of the proximal end of the adjustment member 108, for a snap-fit coupling. Radial alignment for proper assembly of the advancement mechanism is accomplished when an elongated slot 126 formed in the inner surface 109 of the distal end of the member 108 receives the guided member 110 situated in the channel 112 of the member 106. As better illustrated in FIG. 7, the width of the slot is in close conformity to the width of the guided member 110 so that rotation of the adjustment member 108 (shown in broken lines) effectively moves the guided member 110 in the channel 112 of the guide member 106. Anchored to the guided member 110 is the proximal end of the device 46, the adjacent distal portion of which is wound about the guide member 106 in the guide channel 112 and extends into the interior of the barrel 55 from the generally straight distal channel portion 116 on the member 106.

As shown in FIG. 8, the distal end of the guide member 106 is inserted into an enlarged conforming opening 130 at the proximal end of the barrel 55 which has a generally cylindrical hollow interior 132. With coupling of the members 108 and 106, the advancement mechanism 17 forms a passage 133 that communicates with the interior 132 of the barrel 55 and allows components, such as the lead wires 40, the electromagnetic cable 74, and the thermocouple wires 41 and 45 extending proximally through the control handle to pass through the barrel 55. While these components extend through the interior 132 of the barrel 55, the device 46 extends through similarly except toward the proximal end of the barrel 55 which is provided with a passage 138 dedicated to the device 46. Advantageously, the passage 138 is configured for alignment with the generally straight distal guide channel 116 of the guide member 106, so that the device 46 can extend from the interior 132, through the passage 138 and be wound onto the member 106.

To assemble the advancing mechanism 17 on the control handle, the guided member 110 with the proximal end of the device 46 anchored thereto is placed in the channel 112 with the adjacent distal portion of the device 46 wounded in the channels 112 and 116 distally therefrom. The distal end of the member 106 is inserted into the barrel 55. The member 108 is inserted distally over the member 106, with the slot 126 aligned with the guided member 110, until the protrusions 120 of the member 106 lock in the ring recess 122 of the member 108 and the distal end of the member 108 generally abuts with the proximal end of the barrel 55.

In operation to accomplish the advancement and retraction of the device 46, the advancing mechanism 17 can be manipulated by the user through rotation of the adjustment member 108 by means of a knob 140 formed on an outer surface at the proximal end of the member 108. As the user rotates the knob (e.g. clockwise in the illustrated embodiment), the slot 126 on the inner surface 109 is rotated about the longitudinal axis of the member 108 to drive the guided member 110 helically along the guide channel 112 in the distal direction, which in turn distally pushes the device 46 connected to the guided member 110. Such advancement can continue until the guided member 110 reaches the generally straight distal guide channel 116, at which location the distal end of the slot 126 blocks further distal movement of the guided member 110.

To retract the device 46, the user rotates the knob 140 in the opposite direction (e.g., counterclockwise in the illustrated embodiment) which causes the slot 126 to drive the guided member 110 helically in the proximal direction, which in turn draws the device 46 proximally. This retraction can continue until the guided member 110 reaches the generally straight proximal guide channel 116, at which location the proximal end of the slot 126 prevents further proximal movement of the guided member 110.

It is understood by one of ordinary skill in the art that an overlapping longitudinal region between the slot 126 and the helical guide channel 112 defines the possible travel distance of the guided member 110 and thus the advancement/retraction distance of the device 46, and therefore variations in either or both of the length of the slot and the longitudinal spread of the channel 112 as between channels 116 and 118, and/or the degree of overlap can alter the travel distance of the guided member 110 and the maximum advancement/retraction distance of the device 46. It is further understood that other variations, including a change in the diameter of the guiding member 106 (which changes the circumference of the helical channel 112 and the maximum advancement/retraction distance) and/or the number of windings or turns of the helical channel can also alter the travel distance and maximum advancement/retraction distance.

The illustrated embodiment of FIG. 3A discloses a needle as the device 46, which can be advance beyond the distal end of the tip electrode 36. Clearly, as understood by one of ordinary skill in the art, the device can be other instruments or structures that need not extend beyond the distal tip of the tip electrode when advanced to its maximum distal position. Indeed, the amount of advancement and retraction desired or appropriate can be achieved with modifications of the advancement mechanism, including but not limited to the aforementioned variations.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the advancing mechanism may be integrated anywhere along the control handle. User interface may be modified to allow for a linear motion deflection knob rather than the rotational knob mentioned above.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
a catheter body;
a device extending through the catheter body and having proximal and distal ends;
a puller wire extending through the catheter body and having proximal and distal ends;
a control handle proximal the catheter body, the control handle comprising:
a distal barrel, the puller wire being anchored at its proximal end in the distal barrel;
a proximal barrel proximal of the distal barrel, the device extending through the distal barrel and terminating at its proximal end in the proximal barrel; and
an advancing mechanism mounted in the proximal barrel and comprising a threaded member, an adjustment member surrounding the threaded member, and a guided member between the threaded member and the adjustment member, the proximal end of the device being connected to the guided member, and the adjustment member being configured to guide the guided member to move in a space between the threaded member and the adjustment member to thereby advance and retract the device.

2. The catheter according to claim 1, wherein each of the threaded member and the adjustment member has a generally cylindrical configuration, the threaded member has an outer surface configured with a helical guide channel, and the adjustment member is configured to guide the guided member to move within the helical guide channel to advance and retract the device.

3. The catheter according to claim 1, wherein the adjustment member is rotatable over the threaded member by a user to control advancement and retraction of the device.

4. The catheter of claim 3, wherein the adjustment member is configured to rotate about a longitudinal axis of the control handle.

5. The catheter according to claim 1, wherein the device is a stiffener wire or a needle.

6. The catheter according to claim 1, wherein the adjustment member has an inner surface with a slot configured to guide movement of the guided member in a guide channel formed in an outer surface of the threaded member.

7. The catheter according to claim 1, wherein a distal end of the advancing mechanism is located at a proximal end of the control handle, and the adjustment member is mounted over the threaded member.

8. The catheter according to claim 1, wherein the control handle further comprises a piston housed in a piston chamber in the distal barrel, and the device extends through the piston into the proximal barrel.

9. The catheter according to claim 8, wherein the puller wire extends through the piston and is anchored at its proximal end to the distal barrel at a location proximal of the piston chamber.

10. The catheter according to claim 1, wherein the device is wound about the threaded member and adapted to unwind and rewind as guided by the threaded member in response to rotation by a user of the adjustment member relative to the threaded member.

11. The catheter according to claim 1, wherein the control handle has a distal region and a proximal region, the control handle having a thumb control in its distal region configured to manipulate the puller wire, and the advancing mechanism in its proximal region.

12. A catheter comprising:
a catheter body;
a puller wire extending through the catheter body and having proximal and distal ends;
a control handle proximal the catheter body, the control handle comprising:
a distal barrel, the puller wire being anchored at its proximal end in the distal barrel;
a proximal barrel proximal of the distal barrel; and an advancing mechanism mounted in the proximal barrel and having a threaded member having a threaded outer circumference defining a channel, an adjustment member mounted onto the threaded member and a guided member situated between the adjustment member and the threaded member; and a device having proximal and distal ends, the proximal end of the device being connected to the guided member, the device extending distally from the guided member through a piston in the control handle and the catheter body, the adjustment member being configured to guide the guided member to move within the channel to wind and unwind the device in the channel to thereby advance and retract the device.

13. The catheter according to claim 12, wherein the adjustment member is configured for rotation relative to the threaded member in one direction to advance the device and in an opposite direction to retract the device.

14. The catheter according to claim 13, wherein the adjustment member is configured to rotate about a longitudinal axis of the control handle.

15. The catheter according to claim 12, wherein each of the threaded member and the adjustment member has a generally cylindrical configuration.

16. A catheter comprising:
    a catheter body having an outer wall, proximal and distal ends and a lumen extending therethrough;
    a puller wire extending through the lumen of the catheter body and having proximal and distal ends;
    a control handle proximal of the catheter body and comprising:
        a distal barrel, the puller wire being anchored at its proximal end in the distal barrel; and
        a proximal barrel proximal of the distal barrel, in which is situated a threaded member, an adjustment member mounted on the threaded member and a guided member situated between the adjustment member and the threaded member; and
    a device connected to the guided member and extending distally from the guided member through the distal barrel of the control handle and the catheter body, the adjustment member being configured for rotation relative to the threaded member to move the guided member in a space between the threaded member and the adjustment member to thereby advance and retract the device.

17. The catheter according to claim 16, wherein a proximal portion of the device is wound about the threaded member and configured to unwind and rewind following movement of the guided member in response to rotation of the adjustment member relative to the threaded member by a user.

18. The catheter according to claim 16, wherein the adjustment member is configured to rotate about a longitudinal axis of the control handle.

19. The catheter according to claim 16, wherein the device is a stiffener wire or a needle.

20. The catheter according to claim 16, further comprising a tip section distal of the catheter body, the device being configured for tissue contact separately from the tip section.

\* \* \* \* \*